(12) United States Patent
Sippy

(10) Patent No.: US 11,000,534 B1
(45) Date of Patent: May 11, 2021

(54) DEUTERATED DERIVATIVES OF PSILOCYBIN AND USES THEREOF

(71) Applicant: Lennham Pharmaceuticals, Inc., Acton, MA (US)

(72) Inventor: Bradford Sippy, Acton, MA (US)

(73) Assignee: Lennham Pharmaceuticals, Inc., Acton, MA (US)

(*) Notice: Subject to any disclaimer, the term of this patent is extended or adjusted under 35 U.S.C. 154(b) by 0 days.

(21) Appl. No.: 17/117,916

(22) Filed: Dec. 10, 2020

Related U.S. Application Data

(60) Provisional application No. 63/106,662, filed on Oct. 28, 2020, provisional application No. 63/089,396, filed on Oct. 8, 2020.

(51) Int. Cl.
*A61K 31/675* (2006.01)
*A61K 31/4045* (2006.01)

(52) U.S. Cl.
CPC ........ *A61K 31/675* (2013.01); *A61K 31/4045* (2013.01)

(58) Field of Classification Search
CPC .................. A61K 31/675; A61K 31/4045
See application file for complete search history.

(56) References Cited

U.S. PATENT DOCUMENTS

| | | |
|---|---|---|
| 2019/0192498 A1 | 6/2019 | Stamets |
| 2020/0199161 A1 | 6/2020 | Londesbrough et al. |

OTHER PUBLICATIONS

Toronto Research Chemicals Inc Safety Data Sheet, Version 5.0 for Psilocybin-d4, prepared Aug. 21, 2013, p. 1-4 (Year: 2013).*
Psilocin-D10 solution, Cat No. P-099, CAS No. 1435934-64-7, p. 1-2, retrieved 2021. (Year: 2021).*
STN Reg No. 1435934-64-7, entered into STN Jun. 7, 2013 (Year: 2013).*
Magana, A Tryptamine Comeback: Interest Beyond Illicit Use, 2015, Analytix, vol. 3, Sigma-Aldrich, Psilocin-D10 solution, CAS No. 1435934-64-7, Cat. No. P-099 and P-049. (Year: 2015).*
Blar, J. Med. Chem, 2000, vol. 43, p. 4701-4710. (Year: 2000).*
STN Reg No. 1246819-43-1, entered into STN on Oct. 22, 2010 (Year: 2010).*
Blei et al., "Simultaneous Production of Psilocybin and a Cocktail of b-Carboline Monoamine Oxidase Inhibitors in "Magic" Mushrooms," Chem. Eur. J., 26: 729-734 (2020).
Brown et al., "Pharmacokinetics of Escalating Doses of Oral Psilocybin in Healthy Adults," Clin Pharmacokinet, 56:1543-1554 (2017).
Dinis-Oliveira, "Metabolism of psilocybin and psilocin: clinical and forensic toxicological relevance," Drug Metabolism Reviews, 49(1):84-91 (2017).
Exempt Chemical Preparations List, Drug Enforcement Administration, Nov. 7, 2017 (284 pages).
Halpern, "Hallucinogens and dissociative agents naturally growing in the United States," Pharmacology & Therapeutics, 102: 131-138 (2004).
Psilocin-D10, Item Details, Cerilliant Analytical Reference Standards (2020).
Psilocin-d4 Stable Isotopes, CAT No. CS-T-93519 (2020).
Psilocybin-d4, Chemical properties, CAS:1246819-43-1 (2020).

* cited by examiner

*Primary Examiner* — Karen Cheng
(74) *Attorney, Agent, or Firm* — Foley Hoag LLP; David P. Halstead; David S. Surry

(57) ABSTRACT

Provided herein are pharmaceutical compositions comprising deuterated derivatives of psilocybin. The provided compositions may be useful for treating and/or preventing various diseases and conditions, such as mood or psychiatric disorders.

12 Claims, No Drawings

DEUTERATED DERIVATIVES OF PSILOCYBIN AND USES THEREOF

RELATED APPLICATIONS

This application claims the benefit of priority to U.S. Provisional Patent Application No. 63/106,662, filed Oct. 28, 2020, and U.S. Provisional Patent Application No. 63/089,396, filed Oct. 8, 2020, the contents of each of which is incorporated by reference herein in its entirety.

BACKGROUND

Psilocybin is a tryptamine alkaloid, which may be isolated from various genera of fungi including the genus *Psilocybe*. Psilocybin is known to have hallucinogenic, anxiolytic, and psychoactive activities. In vivo, psilocybin is rapidly dephosphorylated into the active compound psilocin, which activates serotonin 2A (5-HT2A) receptors in the central nervous system (CNS), mimicking the effects of serotonin.

Psilocybin has been investigated as a potential treatment for anxiety and depression in life-threatening diseases, depression, obsessive-compulsive disorder, alcoholism and nicotine addiction, cluster headaches and autism. However, psilocybin is considered an illegal drug in most countries and is currently a "Schedule I" substance in the United States, like heroin and LSD.

There is a long felt need for safe and effective pharmacotherapies, especially for severe depression, treatment resistant depression, and psychological distress related with life-threatening diseases. It has been surprisingly discovered that the compositions and methods described herein are superior to existing psilocybin-based therapies that have been investigated or are in development to address this long felt need. In addition, it has been surprisingly discovered that deuteration is particularly advantageous for controlled substances, such as psilocybin, as the labeled nature of the substance will allow healthcare providers and law enforcement to distinguish (e.g. by analytical methods) use of a regulated drug product containing the substance from illegal uses, e.g., the consumption of mushrooms containing psilocybin.

SUMMARY OF THE INVENTION

The present invention relates to compositions (e.g., pharmaceutical compositions) comprising deuterated derivatives of psilocybin ([3-[2-(dimethylamino)ethyl]-1H-indol-4-yl] dihydrogen phosphate), including deuterated forms of its active metabolite, psilocin (4-hydroxy-N,N-dimethyltryptamine). In certain embodiments, the composition is suitable for oral administration or consumption. In certain embodiments, the composition is suitable for intravenous (IV) administration. In certain embodiments, the composition is suitable for inhalation or delivery to the lungs. In certain embodiments, the composition is administered using an electronic cigarette or other vaping device, a nebulizer, a pressurized metered dose inhaler (pMDI), or a dry powder inhaler (DPI). In certain embodiments, the composition is a solid dose composition (e.g., tablet, capsule, granule, powder, sachet, or chewable), solution, suspension, or transdermal patch. Also provided herein are kits containing the compositions and instructions for use. Further provided herein are use of the compositions described herein for treating a disease, preventing a disease, treating a condition, and/or preventing a condition.

The compositions described herein comprise deuterated psilocybin and deuterated psilocin. In certain embodiments, the composition comprises a compound of Formula (I):

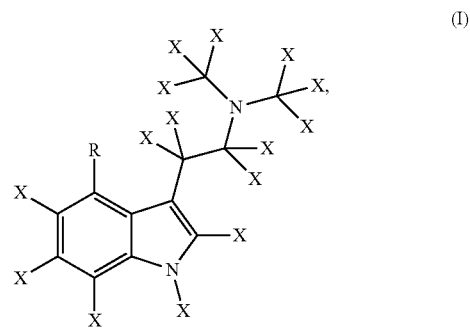

(I)

or a pharmaceutically acceptable salt, prodrug, hydrate, or solvate thereof;

wherein R is selected from —OX or

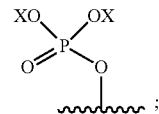

;

each X is independently protium or deuterium; and
at least one X is enriched for deuterium.

In certain embodiments, the composition comprises about 0.5 mg to about 500 mg of a compound of Formula (I), or a pharmaceutically acceptable salt, prodrug, hydrate, or solvate thereof. In certain embodiments, the percentage of the amount of the compound of Formula (I), or a pharmaceutically acceptable salt, prodrug, hydrate, or solvate thereof, relative to the total amount of psilocybin present in the composition ranges from about 1% to about 100%. In another aspect, the composition is for oral administration or consumption. In another aspect, the composition is a solid dose composition (e.g., tablet, capsule, granule, powder, sachet, or chewable). In another aspect, the composition is an oral solution, suspension, oil, or other liquid. In another aspect, the composition is suitable for intravenous (IV) administration. In another aspect, the composition is a topical composition. In another aspect, the composition is a transdermal patch. In another aspect, the composition is suitable for inhalation or delivery to the lungs, nose, or nasal passages. In another aspect, the composition is administered using an electronic cigarette or other vaping device, a nebulizer, a pressurized metered dose inhaler (pMDI), or a dry powder inhaler (DPI).

The disclosure further provides kits comprising one or more compositions described herein and instructions for using the composition(s).

The disclosure further provides methods of delivering the compound of Formula (I), or a pharmaceutically acceptable salt, prodrug, hydrate, solvate, or composition thereof, to a subject in need thereof comprising administering to the subject in need thereof the compound of Formula (I), or a pharmaceutically acceptable salt, prodrug, hydrate, solvate, or composition thereof.

The disclosure further provides methods of treating a disease in a subject in need thereof comprising administering to the subject in need thereof the compound of Formula (I), or a pharmaceutically acceptable salt, prodrug, hydrate, solvate, or composition thereof.

The disclosure further provides methods of preventing a disease in a subject in need thereof comprising administering to the subject in need thereof the compound of Formula (I), or a pharmaceutically acceptable salt, prodrug, hydrate, solvate, or composition thereof.

The disclosure further provides methods of treating a condition in a subject in need thereof comprising administering to the subject in need thereof the compound of Formula (I), or a pharmaceutically acceptable salt, prodrug, hydrate, solvate, or composition thereof.

The disclosure further provides methods of preventing a condition in a subject in need thereof comprising administering to the subject in need thereof the compound of Formula (I), or a pharmaceutically acceptable salt, prodrug, hydrate, solvate, or composition thereof.

In certain embodiments, the subject is a human. In certain embodiments, the subject is an animal.

In another aspect, the side effects experienced after consumption or administration of a compound of Formula (I), or a pharmaceutically acceptable salt, prodrug, hydrate, solvate, or composition thereof, are reduced relative to the administration of its natural (non-isotopically enriched) counterpart at an equivalent dose. In another aspect, the side effect is derealization, visual alteration and distortion, such as halos of light and vivid colors, dilated pupils, dizziness, drowsiness, impaired concentration, muscle weakness, lack of coordination, unusual body sensations, nausea, paranoia, confusion, hallucinations, nausea or vomiting, or yawning. In another aspect, the side effect is increased blood pressure (systolic and diastolic) or increased heart rate.

In another aspect, the consumption or administration of a compound of Formula (I), or a pharmaceutically acceptable salt, prodrug, hydrate, solvate, or composition thereof, results in an increased duration of action, reduction in frequency of administration, increase in patient compliance and/or ease of use relative to the consumption or administration of natural psilocybin at an equivalent dose.

In another aspect, the administration of a compound of Formula (I), or a pharmaceutically acceptable salt, prodrug, hydrate, solvate, or composition thereof, results in a lower, higher, or similar relative magnitude of exposure in plasma, the gastrointestinal tract, and/or the central nervous system (including the brain) as compared to the administration of natural psilocybin at an equivalent dose.

The details of one or more embodiments of the present disclosure are set forth herein. Other features, objects, and advantages of the present disclosure will be apparent from the Detailed Description and Claims.

Definitions

Before further description of the present invention, and in order that the invention may be more readily understood, certain terms are first defined and collected here for convenience.

The terms "composition" and "formulation" are used interchangeably.

The term "total amount of psilocybin" refers to the combined total amount of deuterated psilocybin and natural (non-isotopically enriched) psilocybin.

The term "total amount of psilocin" refers to the combined total amount of deuterated psilocin and natural (non-isotopically enriched) psilocybin The amount of an active agent (e.g., deuterated psilocybin or deuterated psilocin) or combination of active agents thereof included in a provided composition described herein will depend on the target population. In some embodiments, a provided composition contains an effective amount of an active agent (e.g., deuterated psilocybin or deuterated psilocin). The term "effective amount," as used herein, refers to a sufficient amount of the active agent (e.g., deuterated psilocybin or deuterated psilocin) to produce a desired outcome. The exact amount required will vary from subject to subject, depending on the species, age, general condition of the subject, and the indication. The term "therapeutically effective amount" as used herein refers to a sufficient amount of a pharmaceutical agent (e.g., deuterated psilocybin or deuterated psilocin) to achieve the intended purpose, such as, for example, to cause a reduction of symptoms of a condition or disease. A "prophylactically effective amount" refers to a sufficient amount of a pharmaceutical agent (e.g., deuterated psilocybin or deuterated psilocin) to achieve the intended purpose, such as prevention of a condition or disease, one or more symptoms associated with the condition or disease, and/or the recurrence thereof. In certain embodiments, an effective amount of a composition is the effective amount of the active agent (e.g., deuterated psilocybin or deuterated psilocin) included in the composition.

The phrase "same or equivalent amount" as used herein refers to amounts as measured by mass or by moles, respectively.

The term "deuterated" refers to a compound or substituent in which one or more protium ($^1H$) atom(s) is/are replaced by one or more deuterium atom(s) and in which the abundance of deuterium at each deuterated position of the compound is higher than the natural abundance of deuterium, which is about 0.015%. The terms "is deuterium" and "are deuterium" refers to atom(s) in a compound in which one or more protium ($^1H$) atom(s) is/are replaced by one or more deuterium atom(s). A deuterated compound or substituent is considered to be "enriched for deuterium" when the abundance of deuterium at at least one position is higher than the natural abundance of deuterium, which is about 0.015%. In a deuterated compound, the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

Reference to deuterated psilocybin or deuterated psilocin herein (i.e., a compound of Formula (I)) or a pharmaceutically acceptable salt, prodrug, hydrate, or solvate thereof, includes all amorphous and polymorph forms.

Instances of deuterium in a chemical compound provided herein may be shown through the use of the letter "D".

DETAILED DESCRIPTION OF CERTAIN EMBODIMENTS OF THE INVENTION

The present invention relates to compositions a compound of Formula (I). Also provided herein are kits containing the compositions and instructions for use. Further provided herein are uses of any of the compounds or compositions described herein for treating a disease, preventing a disease, treating a condition, preventing a condition, and/or causing an effect.

Compositions, Kits, and Administration

In one aspect, the invention provides a pharmaceutical composition comprising a compound of Formula (I):

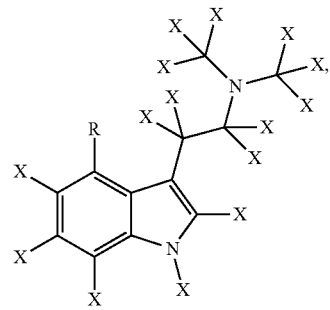

(I)

or a pharmaceutically acceptable salt, prodrug, hydrate, or solvate thereof;

wherein R is selected from —OX or

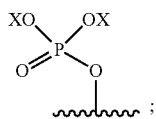

each X is independently protium or deuterium; and at least one X is enriched for deuterium.

Compounds of Formula (I) may comprise stable isotopes of carbon, nitrogen, and oxygen in amounts greater than their natural abundance. For example, one or more carbon atoms may be enriched with $^{13}C$ in an amount greater than about 1.1% (e.g., 1.2-1.5%, 1.5-2%, 2-10%, or more than 10%). One or more nitrogen atoms may be enriched with $^{15}N$ in an amount greater than about 0.4% (e.g., 0.5-1%, 1-2%, 2-10%, or greater than 10%). Likewise, one or more oxygen atoms may be enriched with $^{16}O$ in an amount greater than about 0.24% (e.g., 0.25-0.5%, 0.5-1%, 1-2%, 2-10%, or greater than 10%). Recitation of "hydrogen" or "H" should be understood to encompass $^{1}H$ (protium), $^{2}H$ (deuterium), and $^{3}H$ (tritium) unless otherwise specified.

In one aspect, the compound of Formula (I) is a compound of Formula (IA):

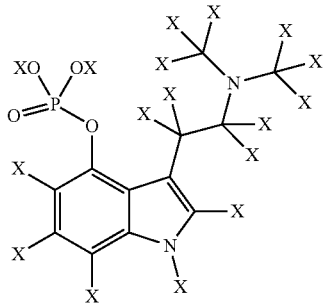

(IA)

or a pharmaceutically acceptable salt, prodrug, hydrate, or solvate thereof;

wherein each X is independently protium or deuterium; and at least one X is enriched for deuterium.

In one aspect, the compound of Formula (I) is a compound of Formula (IB):

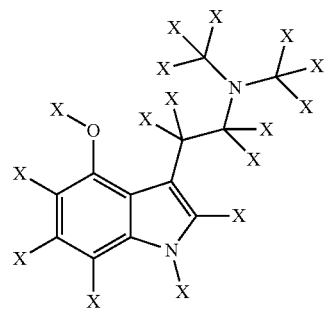

(IB)

or a pharmaceutically acceptable salt, prodrug, hydrate, or solvate thereof;

wherein each X is independently protium or deuterium; and at least one X is enriched for deuterium.

In one aspect, the compound of Formula (I) is a compound of Formula (IC):

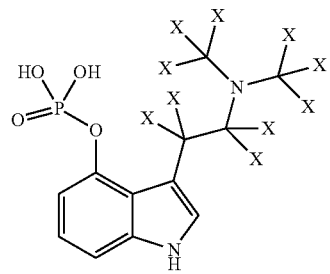

(IC)

or a pharmaceutically acceptable salt, prodrug, hydrate, or solvate thereof;

wherein each X is independently protium or deuterium; and at least one X is enriched for deuterium.

In one aspect, the compound of Formula (I) is a compound of Formula (ID):

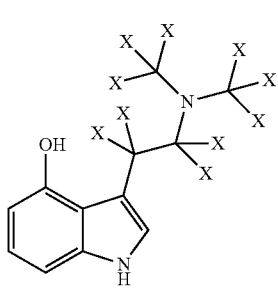

(ID)

or a pharmaceutically acceptable salt, prodrug, hydrate, or solvate thereof;

wherein each X is independently protium or deuterium; and at least one X is enriched for deuterium.

In one aspect, the compound of Formula (I) is a compound of Formula (IE):

(IE)

[Structure: 4-phosphoryloxy indole with ethylamine bearing X-substituted methyl groups]

or a pharmaceutically acceptable salt, prodrug, hydrate, or solvate thereof;
wherein each X is independently protium or deuterium; and
at least one X is enriched for deuterium.

In one aspect, the compound of Formula (I) is a compound of Formula (IF):

(IF)

[Structure: 4-hydroxy indole with ethylamine bearing X-substituted methyl groups]

or a pharmaceutically acceptable salt, prodrug, hydrate, or solvate thereof;
wherein each X is independently protium or deuterium; and
at least one X is enriched for deuterium.

In the pharmaceutical compositions comprising a compound of Formula (IA), at least one instance of X in the compound of Formula (IA) is deuterium. In certain embodiments, at least two instances of X of the compound of Formula (IA) are deuterium. In certain embodiments, at least three instances of X of the compound of Formula (IA) are deuterium. In certain embodiments, at least four instances of X of the compound of Formula (IA) are deuterium. In certain embodiments, at least five instances of X of the compound of Formula (IA) are deuterium. In certain embodiments, at least six instances of X of the compound of Formula (IA) are deuterium. In certain embodiments, at least seven instances of X of the compound of Formula (IA) are deuterium. In certain embodiments, at least eight instances of X of the compound of Formula (IA) are deuterium. In certain embodiments, at least nine instances of X of the compound of Formula (IA) are deuterium. In certain embodiments, at least ten instances of X of the compound of Formula (IA) are deuterium. In certain embodiments, at least eleven instances of X of the compound of Formula (IA) are deuterium. In certain embodiments, at least twelve instances of X of the compound of Formula (IA) are deuterium. In certain embodiments, at least thirteen instances of X of the compound of Formula (IA) are deuterium. In certain embodiments, at least fourteen instances of X of the compound of Formula (IA) are deuterium. In certain embodiments, at least fifteen instances of X of the compound of Formula (IA) are deuterium. In certain embodiments, at least sixteen instances of X of the compound of Formula (IA) are deuterium. In certain embodiments, all instances of X of the compound of Formula (IA) are deuterium.

In the pharmaceutical compositions comprising a compound of Formula (IB), at least one instance of X in the compound of Formula (IB) is deuterium. In certain embodiments, at least two instances of X of the compound of Formula (IB) are deuterium. In certain embodiments, at least three instances of X of the compound of Formula (IB) are deuterium. In certain embodiments, at least four instances of X of the compound of Formula (IB) are deuterium. In certain embodiments, at least five instances of X of the compound of Formula (IB) are deuterium. In certain embodiments, at least six instances of X of the compound of Formula (IB) are deuterium. In certain embodiments, at least seven instances of X of the compound of Formula (IB) are deuterium. In certain embodiments, at least eight instances of X of the compound of Formula (IB) are deuterium. In certain embodiments, at least nine instances of X of the compound of Formula (IB) are deuterium. In certain embodiments, at least ten instances of X of the compound of Formula (IB) are deuterium. In certain embodiments, at least eleven instances of X of the compound of Formula (IB) are deuterium. In certain embodiments, at least twelve instances of X of the compound of Formula (IB) are deuterium. In certain embodiments, at least thirteen instances of X of the compound of Formula (IB) are deuterium. In certain embodiments, at least fourteen instances of X of the compound of Formula (IB) are deuterium. In certain embodiments, at least fifteen instances of X of the compound of Formula (IB) are deuterium. In certain embodiments, all instances of X of the compound of Formula (IB) are deuterium.

In the pharmaceutical compositions comprising a compound of Formula (IC), at least one instance of X in the compound of Formula (IC) is deuterium. In certain embodiments, at least two instances of X of the compound of Formula (IC) are deuterium. In certain embodiments, at least three instances of X of the compound of Formula (IC) are deuterium. In certain embodiments, at least four instances of X of the compound of Formula (IC) are deuterium. In certain embodiments, at least five instances of X of the compound of Formula (IC) are deuterium. In certain embodiments, at least six instances of X of the compound of Formula (IC) are deuterium. In certain embodiments, at least seven instances of X of the compound of Formula (IC) are deuterium. In certain embodiments, at least eight instances of X of the compound of Formula (IC) are deuterium. In certain embodiments, at least nine instances of X of the compound of Formula (IC) are deuterium. In certain embodiments, at least ten instances of X of the compound of Formula (IC) are deuterium. In certain embodiments, all instances of X of the compound of Formula (IC) are deuterium.

In the pharmaceutical compositions comprising a compound of Formula (ID), at least one instance of X in the compound of Formula (ID) is deuterium. In certain embodiments, at least two instances of X of the compound of Formula (ID) are deuterium. In certain embodiments, at least three instances of X of the compound of Formula (ID) are deuterium. In certain embodiments, at least four instances of X of the compound of Formula (ID) are deuterium. In certain embodiments, at least five instances of X of the compound of Formula (ID) are deuterium. In certain embodiments, at least six instances of X of the compound of Formula (ID) are deuterium. In certain embodiments, at least seven instances of X of the compound of Formula (ID) are deuterium. In certain embodiments, at least eight instances of X of the compound of Formula (ID) are deuterium. In certain embodiments, at least nine instances of X of the compound of Formula (ID) are deuterium. In certain embodiments, at least ten instances of X of the compound of Formula (ID) are deuterium. In certain embodiments, all instances of X of the compound of Formula (ID) are deuterium.

In the pharmaceutical compositions comprising a compound of Formula (IE), at least one instance of X in the compound of Formula (IE) is deuterium. In certain embodiments, at least two instances of X of the compound of Formula (IE) are deuterium. In certain embodiments, at least three instances of X of the compound of Formula (IE) are deuterium. In certain embodiments, at least four instances of X of the compound of Formula (IE) are deuterium. In certain embodiments, at least five instances of X of the compound of Formula (IE) are deuterium. In certain embodiments, at least six instances of X of the compound of Formula (IE) are deuterium. In certain embodiments, all instances of X of the compound of Formula (IE) are deuterium.

In the pharmaceutical compositions comprising a compound of Formula (IF), at least one instance of X in the compound of Formula (IF) is deuterium. In certain embodiments, at least two instances of X of the compound of Formula (IF) are deuterium. In certain embodiments, at least three instances of X of the compound of Formula (IF) are deuterium. In certain embodiments, at least four instances of X of the compound of Formula (IF) are deuterium. In certain embodiments, at least five instances of X of the compound of Formula (IF) are deuterium. In certain embodiments, at least six instances of X of the compound of Formula (IF) are deuterium. In certain embodiments, all instances of X of the compound of Formula (IF) are deuterium.

In one aspect, at least one instance of X in the 2-(dimethylamino)ethyl group of the compound of Formula (I) is deuterium. In one aspect, at least two instances of X in the 2-(dimethylamino)ethyl group of the compound of Formula (I) are deuterium. In one aspect, at least three instances of X in the 2-(dimethylamino)ethyl group of the compound of Formula (I) are deuterium. In one aspect, at least four instances of X in the 2-(dimethylamino)ethyl group of the compound of Formula (I) are deuterium. In one aspect, at least five instances of X in the 2-(dimethylamino)ethyl group of the compound of Formula (I) are deuterium. In one aspect, at least six instances of X in the 2-(dimethylamino)ethyl group of the compound of Formula (I) are deuterium. In one aspect, at least seven instances of X in the 2-(dimethylamino)ethyl group of the compound of Formula (I) are deuterium. In one aspect, at least eight instances of X in the 2-(dimethylamino)ethyl group of the compound of Formula (I) are deuterium. In one aspect, at least nine instances of X in the 2-(dimethylamino)ethyl group of the compound of Formula (I) are deuterium. In one aspect, all instances of X in the 2-(dimethylamino)ethyl group of the compound of Formula (I) are deuterium. In one aspect, all instances of X in the dimethylamino group are deuterium. In one aspect, one methyl group within the dimethylamino group is fully deuterated. In one aspect, both methyl groups within the dimethylamino group are fully deuterated.

Specific, non-limiting embodiments of compounds of Formula (IA) and Formula (IB) are provided below. In certain embodiments, the compound of Formula (IA) is a compound selected from:

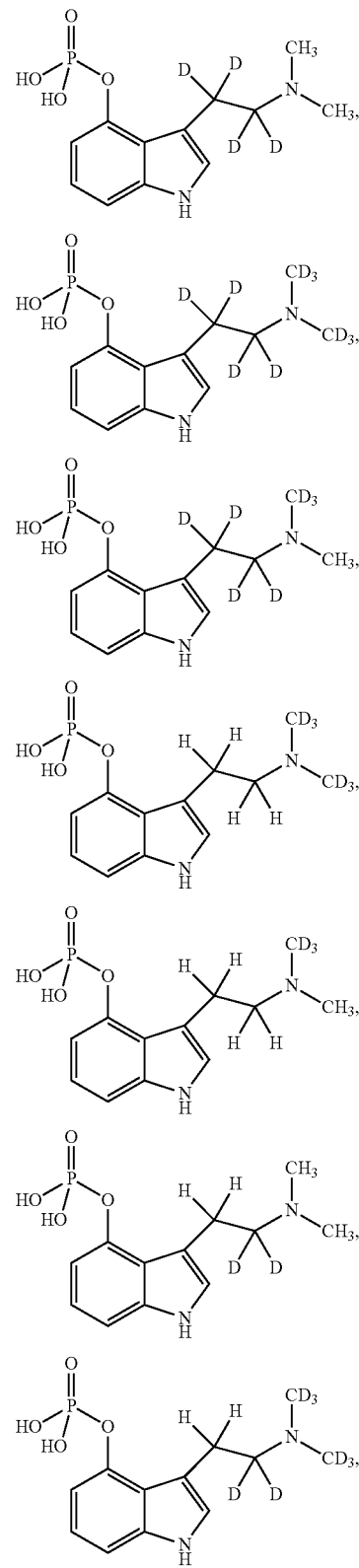

-continued
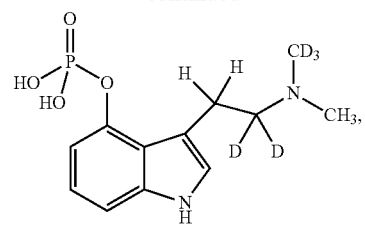
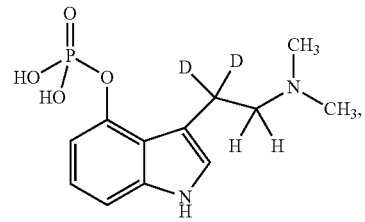
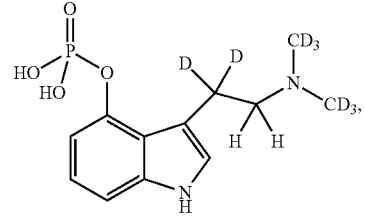
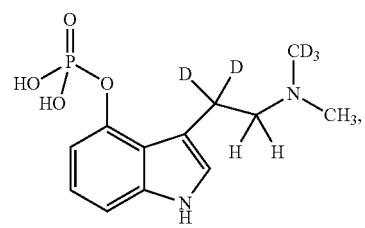
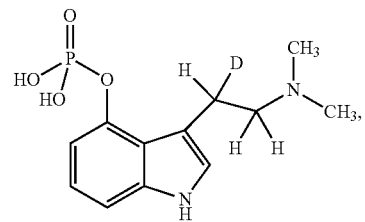
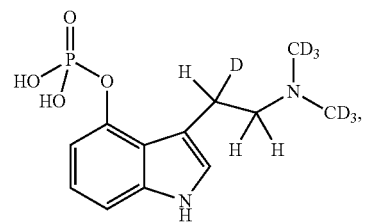
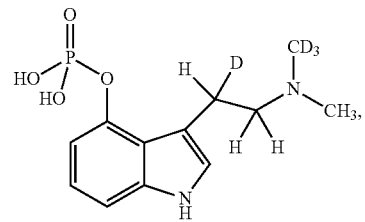
-continued
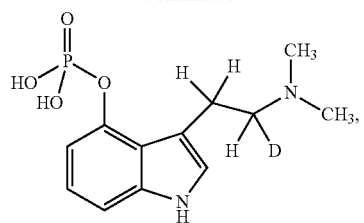
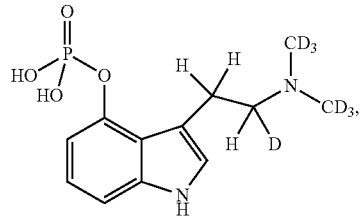
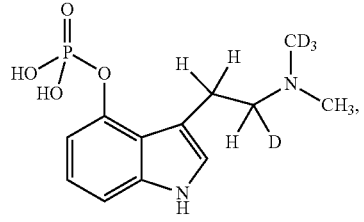
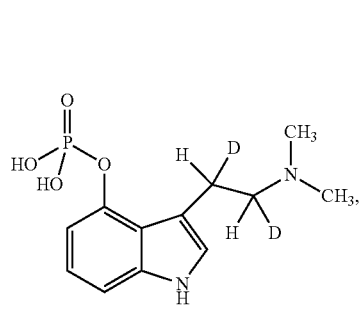
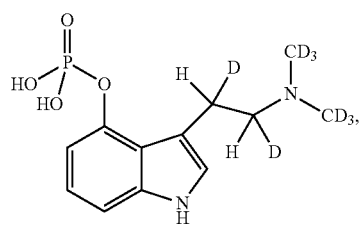
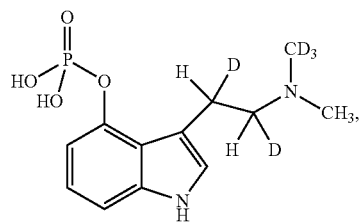
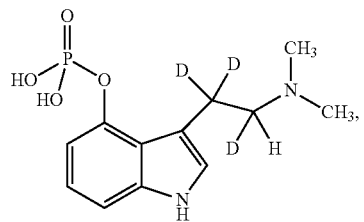

-continued

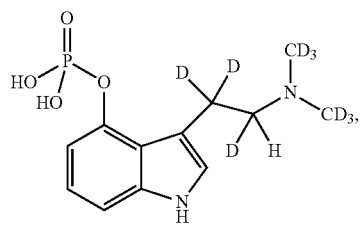

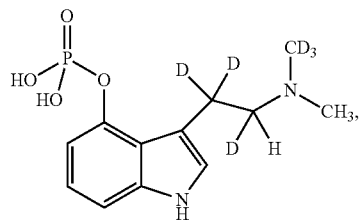

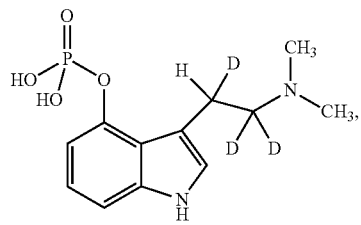

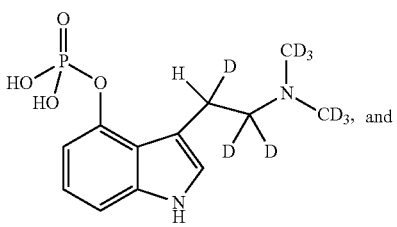

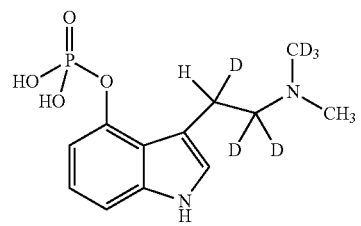

or a pharmaceutically acceptable salt, prodrug, hydrate, or solvate thereof.

In certain embodiments, the compound of Formula (IA) is a compound of Formula (IA-1) or a pharmaceutically acceptable salt, prodrug, hydrate, or solvate thereof:

(IA-1)

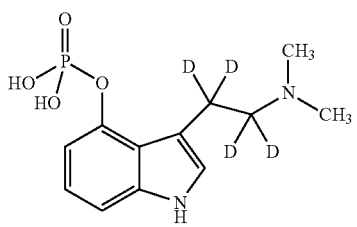

In certain embodiments, the compound of Formula (IA) is a compound of Formula (IA-2) or a pharmaceutically acceptable salt, prodrug, hydrate, or solvate thereof:

(IA-2)

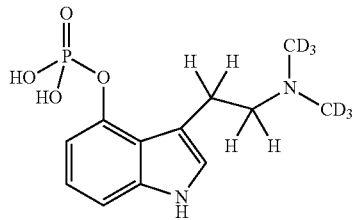

In certain embodiments, the compound of Formula (IA) is a compound of Formula (IA-3) shown below or a pharmaceutically acceptable salt, prodrug, hydrate, or solvate thereof:

(IA-3)

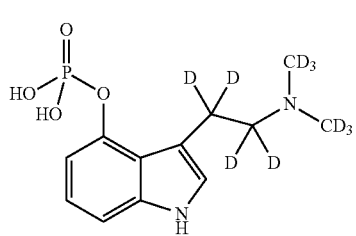

In certain embodiments, the compound of Formula (IB) is a compound selected from:

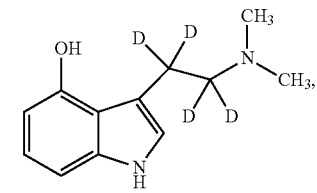

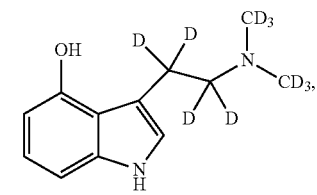

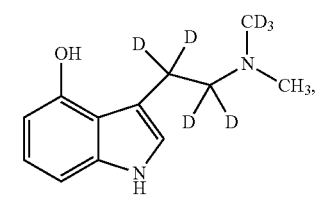

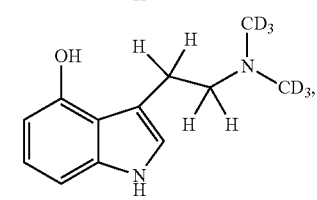

-continued

-continued

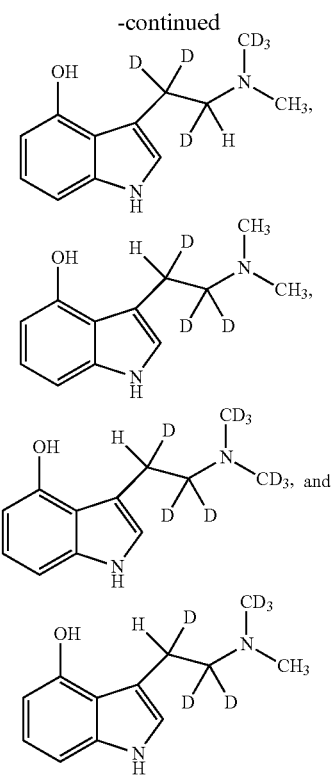

or a pharmaceutically acceptable salt, prodrug, hydrate, or solvate thereof.

In certain embodiments, the compound of Formula (IB) is a compound of Formula (IB-1) shown below or a pharmaceutically acceptable salt, hydrate, or solvate thereof:

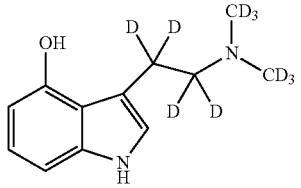

(IB-1)

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

In another aspect, the compound of Formula (I), or a pharmaceutically acceptable salt, prodrug, hydrate, or solvate thereof, has an isotopic purity of at least 50.0%, 60.0%, 70.0%, 75.0%, 80.0%, 85.0%, 90.0%, 95.0%, 97.0%, 98.0%, 99.0%, 99.5%, 99.7%, 99.8%, 99.9%, or 100%. In any of the pharmaceutical compositions described herein, the compound of Formula (I), or a pharmaceutically acceptable salt, prodrug, hydrate, or solvate thereof, has an isotopic purity of at least 50.0%. In another aspect, the compound of Formula (I), or a pharmaceutically acceptable salt, prodrug, hydrate, or solvate thereof, has an isotopic purity of at least 60.0%. In another aspect, the compound of Formula (I), or a pharmaceutically acceptable salt, prodrug, hydrate, or solvate thereof, has an isotopic purity of at least 70.0%. In another aspect, the compound of Formula (I), or a pharmaceutically acceptable salt, prodrug, hydrate, or solvate thereof, has an isotopic purity of at least 75.0%. In another aspect, the compound of Formula (I), or a pharmaceutically acceptable salt, prodrug, hydrate, or solvate thereof, has an isotopic purity of at least 80.0%. In another aspect, the compound of Formula (I), or a pharmaceutically acceptable salt, prodrug, hydrate, or solvate thereof, has an isotopic purity of at least 85.0%. In another aspect, the compound of Formula (I), or a pharmaceutically acceptable salt, prodrug, hydrate, or solvate thereof, has an isotopic purity of at least 90.0%. In another aspect, the compound of Formula (I), or a pharmaceutically acceptable salt, prodrug, hydrate, or solvate thereof, has an isotopic purity of at least 95.0%. In another aspect, the compound of Formula (I), or a pharmaceutically acceptable salt, prodrug, hydrate, or solvate thereof, has an isotopic purity of at least 97.0%. In another aspect, the compound of Formula (I), or a pharmaceutically acceptable salt, prodrug, hydrate, or solvate thereof, has an isotopic purity of at least 98.0%. In another aspect, the compound of Formula (I), or a pharmaceutically acceptable salt, prodrug, hydrate, or solvate thereof, has an isotopic purity of at least 99.0%. In another aspect, the compound of Formula (I), or a pharmaceutically acceptable salt, prodrug, hydrate, or solvate thereof, has an isotopic purity of at least 99.5%. In another aspect, the compound of Formula (I), or a pharmaceutically acceptable salt, prodrug, hydrate, or solvate thereof, has an isotopic purity of at least 99.7%. In another aspect, the compound of Formula (I), or a pharmaceutically acceptable salt, prodrug, hydrate, or solvate thereof, has an isotopic purity of at least 99.9%. In another aspect, the compound of Formula (I), or a pharmaceutically acceptable salt, prodrug, hydrate, or solvate thereof, is suitable for administration to a human or animal. In another aspect, the compound of Formula (I), or a pharmaceutically acceptable salt, prodrug, hydrate, or solvate thereof, is produced and tested in compliance with the Good Manufacturing Practice (GMP) requirements. For such isotopically-labeled molecules, isotopic enrichment may be described as a percentage indicating the percent of isotopic atoms at a particular site on the molecule. The percentage can be referred to as the "isotopic purity" of the isotopically-labeled compound.

Isotopic variants of the compounds of Formula (I) can generally be prepared by methods known to a person skilled in the art, e.g., by substituting a reagent with a deuterium-containing reagent. Depending on the desired sites of deuteration, in some cases deuterium from $D_2O$ or $D_2$ can be incorporated either directly into the compounds or into reagents that are useful for synthesizing such compounds.

In another aspect, any of the pharmaceutical compositions described herein comprise about 0.5 mg to about 250 mg of the compound of Formula (I), or a pharmaceutically acceptable salt, prodrug, hydrate, or solvate thereof. In another aspect, any of the pharmaceutical compositions described herein comprise about 1 mg to about 200 mg of the compound of Formula (I), or a pharmaceutically acceptable salt, prodrug, hydrate, or solvate thereof. In another aspect, any of the pharmaceutical compositions described herein comprise about 5 mg to about 200 mg of the compound of Formula (I), or a pharmaceutically acceptable salt, prodrug, hydrate, or solvate thereof. In another aspect, the pharmaceutical composition comprises about 5 mg to about 100 mg of the compound of Formula (I), or a pharmaceutically acceptable salt, prodrug, hydrate, or solvate thereof. In another aspect, the pharmaceutical composition comprises about 5 mg to about 50 mg of the compound of Formula (I), or a pharmaceutically acceptable salt, prodrug, hydrate, or solvate thereof. In another aspect, the pharmaceutical composition comprises about 10 mg to about 50 mg of the compound of Formula (I), or a pharmaceutically acceptable salt, prodrug, hydrate, or solvate thereof. In another aspect, the pharmaceutical composition comprises about 10 mg to about 25 mg of the compound of Formula (I), or a pharmaceutically acceptable salt, prodrug, hydrate, or solvate thereof.

In another aspect, any of the pharmaceutical compositions described herein comprises about 0.5 mg to about 500 mg of psilocybin comprising a greater than naturally occurring amount of the compound of Formula (IA), or a pharmaceutically acceptable salt, prodrug, hydrate, or solvate thereof. In another aspect, any of the pharmaceutical compositions described herein comprises about 1 mg to about 250 mg of psilocybin comprising a greater than naturally occurring amount of the compound of Formula (IA), or a pharmaceutically acceptable salt, prodrug, hydrate, or solvate thereof. In another aspect, any of the pharmaceutical compositions described herein comprises about 5 mg to about 200 mg of psilocybin comprising a greater than naturally occurring amount of the compound of Formula (IA), or a pharmaceutically acceptable salt, prodrug, hydrate, or solvate thereof. In another aspect, the pharmaceutical composition comprises about 5 mg to about 100 mg of psilocybin comprising a greater than naturally occurring amount of the compound of Formula (IA), or a pharmaceutically acceptable salt, prodrug, hydrate, or solvate thereof. In another aspect, the pharmaceutical composition comprises about 5 mg to about 50 mg of psilocybin comprising a greater than naturally occurring amount of the compound of Formula (IA), or a pharmaceutically acceptable salt, prodrug, hydrate, or solvate thereof. In another aspect, the pharmaceutical composition comprise about 10 mg to about 50 mg of psilocybin comprising a greater than naturally occurring amount of the compound of Formula (IA), or a pharmaceutically acceptable salt, prodrug, hydrate, or solvate thereof. In another aspect, the pharmaceutical composition comprises about 10 mg to about 25 mg of psilocybin comprising a greater than naturally occurring amount of the compound of Formula (IA), or a pharmaceutically acceptable salt, prodrug, hydrate, or solvate thereof.

In another aspect, any of the pharmaceutical compositions described herein comprises about 0.5 mg to about 500 mg of psilocin comprising a greater than naturally occurring amount of the compound of Formula (IB), or a pharmaceutically acceptable salt, prodrug, hydrate, or solvate thereof. In another aspect, any of the pharmaceutical compositions described herein comprises about 1 mg to about 250 mg of psilocin comprising a greater than naturally occurring amount of the compound of Formula (IB), or a pharmaceutically acceptable salt, prodrug, hydrate, or solvate thereof. In another aspect, any of the pharmaceutical compositions described herein comprises about 5 mg to about 200 mg of psilocin comprising a greater than naturally occurring amount of the compound of Formula (IB), or a pharmaceutically acceptable salt, prodrug, hydrate, or solvate thereof. In another aspect, the pharmaceutical composition comprises about 5 mg to about 100 mg of psilocin comprising a greater than naturally occurring amount of the compound of Formula (IB), or a pharmaceutically acceptable salt, prodrug, hydrate, or solvate thereof. In another aspect, the pharmaceutical composition comprises about 5 mg to about 50 mg of psilocin comprising a greater than naturally occurring amount of the compound of Formula (IB), or a pharmaceutically acceptable salt, prodrug, hydrate, or solvate thereof. In another aspect, the pharmaceutical composition comprise about 10 mg to about 50 mg of psilocin comprising a greater than naturally occurring amount of the compound of Formula (IB), or a pharmaceutically acceptable salt, prodrug, hydrate, or solvate thereof. In another aspect, the pharmaceutical composition comprises about 10 mg to about 25 mg of psilocin comprising a greater than naturally occurring amount of the compound of Formula (IB), or a pharmaceutically acceptable salt, prodrug, hydrate, or solvate thereof.

In another aspect, any of the pharmaceutical compositions described herein comprises about 0.01 mg/ml to about 50 mg/ml of the compound of Formula (I), or a pharmaceutically acceptable salt, prodrug, hydrate, or solvate thereof. In another aspect the pharmaceutical composition comprises about 0.05 mg/ml to about 25 mg/ml of the compound of Formula (I), or a pharmaceutically acceptable salt, prodrug, hydrate, or solvate thereof. In another aspect the pharmaceutical composition comprises about 0.01 mg/ml to about 10 mg/ml of the compound of Formula (I), or a pharmaceutically acceptable salt, prodrug, hydrate, or solvate thereof. In another aspect, the pharmaceutical composition comprises about 0.1 mg/ml to about 5 mg/ml of the compound of Formula (I), or a pharmaceutically acceptable salt, prodrug, hydrate, or solvate thereof. In another aspect, the pharmaceutical composition comprises about 0.1 mg/ml to about 1 mg/ml of the compound of Formula (I), or a pharmaceutically acceptable salt, prodrug, hydrate, or solvate thereof.

In another aspect, any of the pharmaceutical compositions described herein comprises about 0.01 mg/ml to about 50 mg/ml of psilocybin comprising a greater than naturally occurring amount of the compound of Formula (IA), or a pharmaceutically acceptable salt, prodrug, hydrate, or solvate thereof. In another aspect the pharmaceutical composition comprises about 0.05 mg/ml to about 25 mg/ml of psilocybin comprising a greater than naturally occurring amount of the compound of Formula (IA), or a pharmaceutically acceptable salt, prodrug, hydrate, or solvate thereof. In another aspect the pharmaceutical composition comprises about 0.1 mg/ml to about 10 mg/ml of psilocybin comprising a greater than naturally occurring amount of the compound of Formula (IA), or a pharmaceutically acceptable salt, prodrug, hydrate, or solvate thereof. In another aspect, the pharmaceutical composition comprises about 0.1 mg/ml to about 5 mg/ml of psilocybin comprising a greater than naturally occurring amount of the compound of Formula (IA), or a pharmaceutically acceptable salt, prodrug, hydrate, or solvate thereof. In another aspect, the pharmaceutical composition comprises about 0.1 mg/ml to about 1 mg/ml of psilocybin comprising a greater than naturally occurring amount of the compound of Formula (IA), or a pharmaceutically acceptable salt, prodrug, hydrate, or solvate thereof.

In another aspect, any of the pharmaceutical compositions described herein comprises about 0.01 mg/ml to about 50 mg/ml of psilocin comprising a greater than naturally occurring amount of the compound of Formula (IB), or a pharmaceutically acceptable salt, prodrug, hydrate, or solvate thereof. In another aspect the pharmaceutical composition comprises about 0.05 mg/ml to about 25 mg/ml of psilocin comprising a greater than naturally occurring amount of the compound of Formula (IB), or a pharmaceutically acceptable salt, hydrate, or solvate thereof. In another aspect the pharmaceutical composition comprises about 0.1 mg/ml to about 10 mg/ml of psilocin comprising a greater than naturally occurring amount of the compound of Formula (IB), or a pharmaceutically acceptable salt, hydrate, or solvate thereof. In another aspect, the pharmaceutical composition comprises about 0.1 mg/ml to about 5 mg/ml of psilocin comprising a greater than naturally occurring amount of the compound of Formula (IB), or a pharmaceutically acceptable salt, hydrate, or solvate thereof. In another aspect, the pharmaceutical composition comprises about 0.1 mg/ml to about 1 mg/ml of psilocin comprising a greater than naturally occurring amount of the compound of Formula (IB), or a pharmaceutically acceptable salt, hydrate, or solvate thereof.

In another aspect, the pharmaceutical compositions described herein may be administered or consumed in a dose that is based on the weight of the subject. In one aspect, the pharmaceutical composition comprises an effective amount of about 0.05 mg/kg to about 2.0 mg/kg of the compound of Formula (I), or a pharmaceutically acceptable salt, prodrug, hydrate, or solvate thereof. In another aspect the pharmaceutical composition comprises an effective amount of about 0.1 mg/kg to about 1.0 mg/kg of the compound of Formula (I), or a pharmaceutically acceptable salt, prodrug, hydrate, or solvate thereof. In another aspect the pharmaceutical composition comprises about 0.2 mg/kg to about 0.6 mg/kg of the compound of Formula (I), or a pharmaceutically acceptable salt, prodrug, hydrate, or solvate thereof. In another aspect the pharmaceutical composition comprises about 0.3 mg/kg to about 0.5 mg/kg of the compound of Formula (I), or a pharmaceutically acceptable salt, prodrug, hydrate, or solvate thereof.

In any of the pharmaceutical compositions described herein, the compound of Formula (IA), or a pharmaceutically acceptable salt, prodrug, hydrate, or solvate thereof, represents greater than 1%, 2%, 3%, 4%, 5%, 6%, 7%, 8%, 9%, 10%, 15%, 20%, 30%, 40%, 50%, 60%, 70%, 80%, 90%, 95%, 97%, 98%, 99%, 99.5%, 99.7%, 99.9%, 99.95%, 99.99%, or 100% of the total amount of psilocybin present in the composition. In another aspect, the percentage of the amount of the compound of Formula (IA), or a pharmaceutically acceptable salt, prodrug, hydrate, or solvate thereof, relative to the total amount of psilocybin present in the composition is about 1% to about 100%. In another aspect, the percentage of the amount of the compound of Formula (IA), or a pharmaceutically acceptable salt, prodrug, hydrate, or solvate thereof, relative to the total amount of psilocybin present in the composition ranges from about 1% to about 99.99%. In another aspect, the percentage of the amount of the compound of Formula (IA), or a pharmaceutically acceptable salt, prodrug, hydrate, or solvate thereof, relative to the total amount of psilocybin present in the composition ranges from about 10% to about 100%. In another aspect, the percentage of the amount of the compound of Formula (IA), or a pharmaceutically acceptable salt, prodrug, hydrate, or solvate thereof, relative to the total amount of psilocybin present in the composition ranges from about 25% to about 100%. In another aspect, the percentage of the amount of the compound of Formula (IA), or a pharmaceutically acceptable salt, prodrug, hydrate, or solvate thereof, relative to the total amount of psilocybin present in the composition ranges from about 40% to about 100%. In another aspect, the percentage of the amount of the compound of Formula (IA), or a pharmaceutically acceptable salt, prodrug, hydrate, or solvate thereof, relative to the total amount of psilocybin present in the composition ranges from about 50% to about 100%. In another aspect, the percentage of the amount of the compound of Formula (IA), or a pharmaceutically acceptable salt, prodrug, hydrate, or solvate thereof, relative to the total amount of psilocybin present in the composition ranges from about 60% to about 100%. In another aspect, the percentage of the amount of the compound of Formula (IA), or a pharmaceutically acceptable salt, prodrug, hydrate, or solvate thereof, relative to the total amount of psilocybin present in the composition ranges from about 70% to about 100%. In another aspect, the percentage of the amount of the compound of Formula (IA), or a pharmaceutically acceptable salt, prodrug, hydrate, or solvate thereof, relative to the total amount of psilocybin present in the composition ranges from about 80% to about 100%. In another aspect, the percentage of the amount of the compound of Formula (IA), or a pharmaceutically acceptable salt, prodrug, hydrate, or solvate thereof, relative to the total amount of psilocybin present in the composition ranges from about 90% to about 100%.

In any of the pharmaceutical compositions described herein, the compound of Formula (IB), or a pharmaceutically acceptable salt, prodrug, hydrate, or solvate thereof, represents greater than 1%, 2%, 3%, 4%, 5%, 6%, 7%, 8%, 9%, 10%, 15%, 20%, 30%, 40%, 50%, 60%, 70%, 80%, 90%, 95%, 97%, 98%, 99%, 99.5%, 99.7%, 99.9%, 99.95%, 99.99%, or 100% of the total amount of psilocin present in the composition. In another aspect, the percentage of the amount of the compound of Formula (IB), or a pharmaceutically acceptable salt, prodrug, hydrate, or solvate thereof, relative to the total amount of psilocin present in the composition is about 1% to about 100%. In another aspect, the percentage of the amount of the compound of Formula (IB), or a pharmaceutically acceptable salt, prodrug, hydrate, or solvate thereof, relative to the total amount of psilocin present in the composition ranges from about 1% to about 99.99%. In another aspect, the percentage of the amount of the compound of Formula (IB), or a pharmaceutically acceptable salt, prodrug, hydrate, or solvate thereof, relative to the total amount of psilocin present in the composition ranges from about 10% to about 100%. In another aspect, the percentage of the amount of the compound of Formula (IB), or a pharmaceutically acceptable salt, prodrug, hydrate, or solvate thereof, relative to the total amount of psilocin present in the composition ranges from about 25% to about 100%. In another aspect, the percentage of the amount of the compound of Formula (IB), or a pharmaceutically acceptable salt, prodrug, hydrate, or solvate thereof, relative to the total amount of psilocin present in the composition ranges from about 40% to about 100%. In another aspect, the percentage of the amount of the compound of Formula (IB), or a pharmaceutically acceptable salt, prodrug, hydrate, or solvate thereof, relative to the total amount of psilocin present in the composition ranges from about 50% to about 100%. In another aspect, the percentage of the amount of the compound of Formula (IB), or a pharmaceutically acceptable salt, prodrug, hydrate, or solvate thereof, relative to the total amount of psilocin present in the composition ranges from about 60% to about 100%. In another aspect, the percentage of the amount of the compound of Formula (IB), or a pharmaceutically acceptable salt, prodrug, hydrate, or solvate thereof, relative to the total amount of psilocin present in the composition ranges from about 70% to about 100%. In another aspect, the percentage of the amount of the compound of Formula (IB), or a pharmaceutically acceptable salt, prodrug, hydrate, or solvate thereof, relative to the total amount of psilocin present in the composition ranges from about 80% to about 100%. In another aspect, the percentage of the amount of the compound of Formula (IB), or a pharmaceutically acceptable salt, prodrug, hydrate, or solvate thereof, relative to the total amount of psilocin present in the composition ranges from about 90% to about 100%.

In another aspect, the compound of Formula (I), or a pharmaceutically acceptable salt, prodrug, hydrate, or solvate thereof, is included in an amount from about 0.001% to 50% based on the weight of all the components of the composition. In certain embodiments, the compound of Formula (I), or a pharmaceutically acceptable salt, prodrug, hydrate, or solvate thereof, is included in an amount from about 0.1% to 5% (e.g., 0.1% to 1%, 1% to 5%) based on the weight of all the components of the composition. In certain embodiments, the compound of Formula (I), or a pharmaceutically acceptable salt, prodrug, hydrate, or solvate thereof, is included in an amount from about 5% to 20% based on the weight of all the components of the composition. In certain embodiments, the compound of Formula (I), or a pharmaceutically acceptable salt, prodrug, hydrate, or solvate thereof, is included in an amount from about 20% to 50% based on the weight of all the components of the composition.

It will be understood that the total daily usage of the pharmaceutical composition described herein may be decided by an attending physician within the scope of sound medical judgment, and will depend safety and toxicity profile of the components of the pharmaceutical composition. The specific therapeutically effective dose level for any particular patient or organism will depend upon a variety of factors including the disorder being treated and the severity of the disorder; the clinical studies results, the activity of the specific compound employed; the specific pharmaceutical composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, *The Pharmacological Basis of Therapeutics*, Tenth Edition, A. Gilman, J. Hardman, and L. Limbird, eds., McGraw-Hill Press, 155-173, 2001).

In another aspect, any of the pharmaceutical compositions described herein may be suitable for oral administration, parenteral (e.g., intravenous (IV)) administration, topical administration, inhalation, buccal administration, or for delivery to the lungs. In another aspect, the pharmaceutical composition is suitable for oral use, consumption, or administration. In another aspect, the pharmaceutical composition is suitable for parenteral use or administration. In another aspect, the pharmaceutical composition is suitable for intravenous (IV) use or administration. In another aspect, the pharmaceutical composition is suitable for topical administration. In another aspect, the pharmaceutical composition is suitable for inhalation, administration, or delivery to the lungs or nasal passages.

In one aspect, the pharmaceutical compositions described herein may be formulated as set forth in U.S. Pat. No. 10,519,175, the entire disclosure of which is incorporated by reference herein.

In another aspect, any of the pharmaceutical compositions described herein may be suitable for oral consumption, use, or administration. In another aspect, the pharmaceutical composition is in a liquid form such as an oil. In another aspect, the oil is sesame seed oil, avocado oil, olive oil, canola oil, or any other oil suitable for consumption by a mammal. The composition may further comprise dehydrated alcohol.

In another aspect, any of the pharmaceutical compositions described herein suitable for oral administration may be a solid dose composition. In another aspect, the solid dose composition may be a tablet, capsule, granule, powder, sachet, or chewable.

In another aspect, any of the pharmaceutical compositions described herein suitable for topical administration may be a transdermal patch, tincture, or paste.

In another aspect, any of the pharmaceutical compositions described herein suitable for inhalation or delivery to the lungs may be consumed, delivered or administered using an electronic cigarette or other vaping device, a nebulizer, a pressurized metered dose inhaler (pMDI), or a dry powder inhaler (DPI).

In another aspect, any of the pharmaceutical compositions described herein may further comprise a pharmaceutically acceptable carrier.

In certain embodiments, pharmaceutical excipients for an oral formulation include: diluents, such as, microcrystalline cellulose, starch, mannitol, calcium hydrogen phosphate anhydrous or co-mixtures of silicon dioxide, calcium carbonate, microcrystalline cellulose and talc; disintegrants, such as, sodium starch glycolate or croscarmellose sodium; binders, such as, povidone, co-povidone or hydroxyl propyl cellulose; lubricants, such as, magnesium stearate or sodium stearyl fumarate; glidants, such as, colloidal silicon dioxide; and film coats, such as, Opadry II white or PVA based brown Opadry II.

In certain embodiments, the pharmaceutical composition comprises a solid dose composition which comprises a filler. In one aspect, the filler is a silicified filler, preferably a silicified microcrystalline cellulose having a particle size range of from about 45 to 150 microns. In one aspect, the silicified microcrystalline filler may comprise a first filler, having a particle size range of from about 45 to 80 microns in an amount of up to 30%, more preferably up to 20%, more preferably still up to 15% or less and a second filler, having a particle size range of from about 90 to 150 microns, in an amount of up to 70%, more preferably up to 80, and more preferably still up to 85% or more, by weight.

The formulation may further comprise or consist of a disintegrant, preferably sodium starch glycolate, a glidant, preferably colloidal silicon dioxide and a lubricant, preferably sodium stearyl fumarate.

The present disclosure includes the use of zwitterions or pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

In another aspect, any of the pharmaceutical compositions described herein may further comprise an additional agent. In another aspect, the additional agent refers to natural or synthetic compound(s) capable of activity or other direct effect in the diagnosis, cure, mitigation, treatment or prevention of disease or to affect the structure and function of the body. In any of the foregoing embodiments, a provided composition may contain one or more active agents, including, but not limiting to pharmaceutical agent that belong to different Biopharmaceutics Classification System (BCS), for example, from BCS class I, II, III or IV, and/or peptides, and/or vaccines and/or nucleic acid-based products and/or immunologic agents and/or phytopharmaceutical agents and/or nutraceutical agents and/or cosmetic agents and/or supplements. In certain embodiments, the active agent is a small molecule (e.g., when the molecular weight is lower than 500, 800, 1000, or 1500, g/mol). In certain embodiments, the active agent is a drug approved by the U.S. Food and Drug Administration and/or the European Medicines Agency.

In the present invention, each additional agent may be incorporated in the composition. Depending upon the qualitative and quantitative composition of the formulation chosen, the additional agent(s) may be released from the composition over a period of time (i.e. sustained release) or immediately. The present invention can be used in the treatment of both humans and animals.

In another aspect, the additional agent is an anti-depressant, a cannabinoid, a stimulant, an anti-inflammatory agent, a steroid, a barbiturate, an opioid analgesic, a sleep agent (e.g. melatonin or eszopiclone), an anxiolytic, an antipsychotic, or a combination thereof. In another aspect, any of the hydrogen atoms in the anti-depressant, cannabinoid, stimulant, anti-inflammatory agent, steroid, barbiturate, opioid analgesic, sleep agent (e.g. melatonin or eszopiclone), anxiolytic, or antipsychotic may be replaced with deuterium.

In certain embodiments, a provided composition comprises one or more disintegrants or solubilizing agents, such as a cyclodextrin, or a carboxymethyl cellulose, calcium carboxymethyl cellulose, low-substituted hydroxypropyl cellulose, sodium croscarmellose, sodium carboxy starch, calcium carbonate, sodium carbonate and the like.

It will be understood that when a range is recited in the application, the end of the range are specifically disclosed as if specifically recited. For example, a range of about 19% to about 99% specifically include a disclosure separately of 19% and separately of 99%.

Also encompassed by the present disclosure are kits (e.g., pharmaceutical or nutraceutical packs). In certain embodiments, the kit comprises a pharmaceutical or nutraceutical composition described herein, and instructions for using the pharmaceutical or nutraceutical composition. In certain embodiments, the kit comprises a first container, wherein the first container includes the pharmaceutical or nutraceutical composition. In some embodiments, the kit further comprises a second container. In certain embodiments, the second container includes an excipient (e.g., an excipient for dilution or suspension of the pharmaceutical or nutraceutical composition). In certain embodiments, the second container includes an additional agent. In some embodiments, the kit further comprises a third container. In certain embodiments, the third container includes an additional agent. In some embodiments, the pharmaceutical or nutraceutical composition included in the first container and the excipient or additional agent(s) included in the second container are combined to form one unit dosage form. In some embodiments, the pharmaceutical or nutraceutical composition included in the first container, the excipient included in the second container, and the additional agent included in the third container are combined to form one unit dosage form. In certain embodiments, each of the first, second, and third containers is independently a vial, ampule, bottle, syringe, dispenser package, tube, sprayer, or inhaler. In certain embodiments, at least one of the first, second, and third containers is a sprayer.

In certain embodiments, the instructions are for administering the pharmaceutical or nutraceutical composition to a subject in need thereof. In certain embodiments, the instructions comprise information required by a regulatory agency, such as the U.S. Food and Drug Administration (FDA) or the European Agency for the Evaluation of Medicinal Products (EMA). In certain embodiments, the instructions comprise prescribing information.

Methods of Use and Uses

The present disclosure also provides methods of using the compounds and compositions. In another aspect, the present disclosure provides methods of delivering to a subject in need thereof a composition (e.g., an effective amount of the composition) of the present disclosure.

In another aspect, the present disclosure provides methods of treating a disease in a subject in need thereof comprising administering to the subject in need thereof an effective amount (e.g., therapeutically effective amount) of a compound or composition (e.g., pharmaceutical or nutraceutical composition) of the present disclosure.

In another aspect, the present disclosure provides methods of preventing a disease in a subject in need thereof comprising administering to the subject in need thereof an effective amount (e.g., therapeutically effective amount) of a compound or composition (e.g., pharmaceutical or nutraceutical composition) of the present disclosure.

In another aspect, provided herein are uses of the compounds or compositions of the present disclosure in the manufacture of a medicament for use in a method (e.g., method of delivering an active agent to a subject in need thereof, method of treating a disease in a subject in need thereof, method of preventing a disease in a subject in need thereof) of the present disclosure.

In another aspect, provided herein are uses of the compounds or compositions of the present disclosure in a method (e.g., method of delivering an active agent to a subject in need thereof, method of treating a disease in a subject in need thereof, method of preventing a disease in a subject in need thereof) of the present disclosure.

In certain embodiments, the subject is an animal. The animal may be of either sex and may be at any stage of development. In certain embodiments, the subject described herein is a human. The human may be a child or an adult. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a dog. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice, transgenic pigs). In certain embodiments, a subject in need thereof is a subject in need of delivery of an active agent or a composition, a subject in need of treatment of a disease, or a subject in need of prevention of a disease.

In certain embodiments, the effective amount is effective in treating the disease. In certain embodiments, the effective amount is effective in preventing the disease.

In certain aspects, the disease is a neurological disease. In certain embodiments, the disease is a neurological disease. The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including Alzheimer's disease, Parkinson's disease, amyotrophic lateral sclerosis, tauopathies (including frontotemporal dementia), and Huntington's disease. Examples of neurological diseases include headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIAD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofiaromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina *bifida*; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissiale spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

In certain embodiments, the disease is a painful condition. A "painful condition" includes neuropathic pain (e.g., peripheral neuropathic pain), central pain, deafferentation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the disease is a psychiatric disorder. The term "psychiatric disorder" refers to a disease of the mind and includes diseases and disorders listed in the Diagnostic and Statistical Manual of Mental Disorders—Fourth Edition (DSM-IV), published by the American Psychiatric Association, Washington D. C. (1994). Psychiatric disorders include anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

In certain embodiments, the method further comprises administering to the subject in need thereof an additional therapy. In certain embodiments, the additional therapy is an additional pharmaceutical agent. In certain embodiments, the additional therapy is an additional nutraceutical agent.

The pharmaceutical and nutraceutical compositions of the present disclosure and the additional therapy may show synergy in the methods and uses of the present disclosure.

In another aspect, the invention is directed to a method for treating a depressive disorder in a subject in need thereof, the method comprising administering to the subject a composition comprising a compound of Formula I. In certain embodiments, the compound of Formula I is a compound of Formula (IA). In certain embodiments, the compound of Formula (IA) is a compound of Formula (IA-2) or (IA-3) as described herein. In certain embodiments, the depressive disorder is major depressive disorder or treatment-resistant depression.

In another aspect, the invention is directed to a method for treating a mood disorder in a subject in need thereof, the method comprising administering to the subject a composition comprising a compound of Formula (I). In certain embodiments, the compound of Formula (I) is a compound of Formula (IA). In certain embodiments, the compound of Formula (IA) is a compound of Formula (IA-2) or (IA-3) as described herein. In certain embodiments, the mood disorder is psychological distress (e.g., depression or anxiety) related with a life-threatening disease.

In another aspect, the invention is directed to a method for treating an anxiety disorder in a subject in need thereof, the method comprising administering to the subject a composition comprising a compound of Formula (I). In certain embodiments, the compound of Formula (I) is a compound of Formula (IA). In certain embodiments, the compound of Formula (IA) is a compound of Formula (IA-2) or (IA-3) as described herein.

In another aspect, the invention is directed to a method for treating an addiction disorder in a subject in need thereof, the method comprising administering to the subject a composition comprising a compound of Formula (I). In certain embodiments, the compound of Formula (I) is a compound of Formula (IA). In certain embodiments, the compound of Formula (IA) is a compound of Formula (IA-2) or (IA-3) as described herein.

In another aspect, the invention is directed to a method for treating a pain disorder in a subject in need thereof, the method comprising administering to the subject a composition comprising a compound of Formula (I). In certain embodiments, the compound of Formula (I) is a compound of Formula (IA). In certain embodiments, the compound of Formula (IA) is a compound of Formula (IA-2) or (IA-3) as described herein.

In another aspect, the pain disorder is migraine, arthritis, headache, back pain, bursitis, chronic pain, acute pain, musculoskeletal pain, osteoarthritis, psoriatic arthritis, rheumatoid arthritis, or sciatica. In another aspect, the pain disorder is migraine. In another aspect, the pain disorder is arthritis. In another aspect, the pain disorder is headache. In another aspect, the pain disorder is back pain. In another aspect, the pain disorder is bursitis. In another aspect, the pain disorder is chronic pain. In another aspect, the pain disorder is acute pain. In another aspect, the pain disorder is musculoskeletal pain. In another aspect, the pain disorder is osteoarthritis. In another aspect, the pain disorder is psoriatic arthritis. In another aspect, the pain disorder is rheumatoid arthritis. In another aspect, the pain disorder is sciatica. In another aspect, the pain disorder is migraine or headache.

In another aspect, the invention is directed to a method for treating a psychiatric disorder in a subject in need thereof, the method comprising administering to the subject a composition comprising a compound of Formula (I). In certain embodiments, the compound of Formula (I) is a compound of Formula (IA). In certain embodiments, the compound of Formula (IA) is a compound of Formula (IA-2) or (IA-3) as described herein.

In another aspect, the neurological or psychiatric disorder is narcolepsy, Alzheimer's disease, attention deficit hyperactivity disorder (ADHD), schizophrenia, Parkinson's disease, or depression. In another aspect, the neurological or psychiatric disorder is narcolepsy. In another aspect, the neurological or psychiatric disorder is Alzheimer's disease. In another aspect, the neurological or psychiatric disorder is attention deficit hyperactivity disorder (ADHD). In another aspect, the neurological or psychiatric disorder is schizophrenia. In another aspect, the neurological or psychiatric disorder is Parkinson's disease. In another aspect, the neurological or psychiatric disorder is depression.

In another aspect, in any of the methods described herein, the method comprises administering a single dose of a pharmaceutical composition comprising a compound of Formula (I) to treat, prevent, or cure the disease or condition. In another aspect, in any of the methods described herein, the method comprises administering a pharmaceutical composition comprising a compound of Formula (I) in the presence of supportive care, e.g. a healthcare provider, to ensure safe use of the product, to provide emotional support for the patient, and/or to monitor for possible side effects.

In another aspect, the side effects experienced after consumption or administration of a compound of Formula (I), or a pharmaceutically acceptable salt, prodrug, hydrate, solvate, or composition thereof, are reduced relative to the administration of the same compound that is not isotopically enriched at an equivalent dose. In another aspect, the side effect is derealization, visual alteration and distortion, such as halos of light and vivid colors, dilated pupils, dizziness, drowsiness, impaired concentration, muscle weakness, lack of coordination, unusual body sensations, nausea, paranoia, confusion, hallucinations, nausea or vomiting, or yawning.

In another aspect, the plasma half-life (t1/2) of the compound of Formula (I) after administration of the compound of Formula (I), or a pharmaceutically acceptable salt, prodrug, hydrate, or composition thereof, is longer than that of the same compound that is not isotopically enriched at an equivalent dose.

In any of the methods described herein, the plasma half-life (t1/2) of the compound of Formula (I) after administration of the compound of Formula (I), or a pharmaceutically acceptable salt, prodrug, hydrate, or composition thereof, is at least 5%, 10%, 25%, 30%, 35%, 40%, 45%, 50%, 55%, or 60% longer than that of the same compound that is not isotopically enriched at an equivalent dose. In certain embodiments, the plasma half-life (t1/2) of a compound of Formula (IA-2) or (IA-3) as described herein after administration is at least at least 5%, 10%, 25%, 30%, 35%, 40%, 45%, 50%, 55%, or 60% longer than that of non-isotopically enriched psilocybin.

In another aspect, the administration of the compound of Formula (I), or a pharmaceutically acceptable salt, prodrug, hydrate, or composition thereof, results in at least a 1%, 2%, 3%, 4%, 5%, 6%, 7%, 8%, 9%, or 10% reduction in the formation of the psilocin-O-glucuronide metabolite. In one aspect, the metabolite levels are determined at 10, 20, 40, or 60 minutes following administration of the compound of Formula (I).

Example 1

A study was conducted to assess the metabolic stability and metabolite formulation of psilocin and d10-psilocin (the compound of Formula (IB-1)) in human hepatocytes under the conditions set forth in Table 1.

TABLE 1

| Study species | Human (mixed gender, lot HQE, viability 85%) |
|---|---|
| Incubation volume | 300 μL, pH 7.4 Celsis IVT In Vitro GRO KHB medium |
| Sampling volume | 40 μL |
| Cell viability | 1.0 million viable cells/ml |
| DMSO content | 0.5% |
| Incubation time | 0, 10, 20, 40 and 60 min @ 37° C. |
| Replicates | 2 |
| Termination of incubations | 2 - fold volume of cold 75% acetonitrile |
| Storage of the samples | Immediate analysis |
| Test compound concentration | 1 uM |
| Control | Verapamil |

The results of the study are as follows. The half-lives of psilocin and d10-psilocin were calculated to be 178 minutes vs. 298 minutes, respectively. For psilocin, approximately 78% of parent remained after the 60-minute incubation, whereas for d10-psilocin approximately 84% of parent remained after the 60-minute incubation. The major metabolite for both psilocin and d10-psilocin was the reversible metabolite psilocin-O-glucuronide, with approximately 10% of d10-psilocin converting to the glucuronide after 60-minute incubation and approximately 13% of psilocin converting to the glucuronide after 60-minute incubation. The inactive and irreversible metabolite 4-hydroxy-indole-3-acetic acid was undetected after 60-minute incubation of d10-psilocin and approximately 0.1% of psilocin after 60-minute incubation.

Various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising," "including," and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A pharmaceutical composition comprising a deuterated compound of Formula (IA-2) or (IA-3):

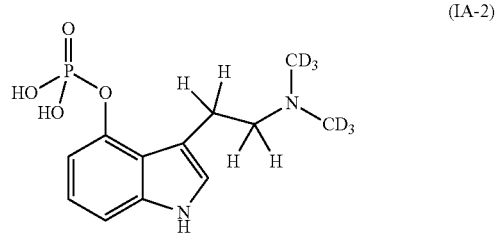 [SMILES: [2H]C([2H])([2H])N(CCc1c[nH]c2cccc(OP(=O)(O)O)c12)C([2H])([2H])[2H]]

(IA-2)

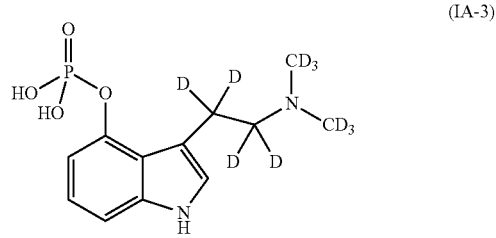 [SMILES: [2H]C([2H])([2H])N(C([2H])([2H])[2H])C([2H])([2H])C([2H])([2H])c1c[nH]c2cccc(OP(=O)(O)O)c12]

(IA-3)

or a pharmaceutically acceptable salt, prodrug, hydrate, or solvate thereof;

wherein the pharmaceutical composition comprises about 0.5 mg to 500 mg of the compound of Formula (IA-2) or (IA-3).

2. The composition of claim 1, wherein the composition further comprises a pharmaceutically acceptable carrier.

3. The composition of claim 2, wherein the composition is suitable for oral administration.

4. The composition of claim 2, wherein the composition is suitable for intravenous (IV) administration.

5. The composition of claim 3, wherein the composition is a solid dose composition.

6. The composition of claim 5, wherein the solid dose composition is a tablet, capsule, granule, powder, sachet, or chewable.

7. The composition of claim 1, wherein the composition comprises about 0.5 mg to about 250 mg of the deuterated compound of Formula (IA-2) or (IA-3), or a pharmaceutically acceptable salt thereof.

8. The composition of claim 7, wherein the composition comprises about 0.5 mg to about 50 mg of the deuterated compound of Formula (IA-2) or (IA-3), or a pharmaceutically acceptable salt thereof.

9. The composition of claim 8, wherein the composition comprises about 10 mg to about 50 mg of the deuterated compound of Formula (IA-2) or (IA-3), or a pharmaceutically acceptable salt thereof.

10. The composition of claim 2, wherein the composition comprises about 0.01 mg/ml to about 50 mg/ml of the deuterated compound of Formula (IA-2) or (IA-3), or a pharmaceutically acceptable salt thereof.

11. The composition of claim 1, wherein the composition comprises the deuterated compound of Formula (IA-2) or (IA-3), or a pharmaceutically acceptable salt or prodrug thereof.

12. The composition of claim 1, wherein the composition comprises the deuterated compound of Formula (IA-2) or (IA-3), or a pharmaceutically acceptable salt thereof.

* * * * *

(12) EX PARTE REEXAMINATION CERTIFICATE (12073rd)
United States Patent
Sippy

(10) Number: US 11,000,534 C1
(45) Certificate Issued: Jun. 16, 2022

(54) DEUTERATED DERIVATIVES OF PSILOCYBIN AND USES THEREOF

(71) Applicant: Lennham Pharmaceuticals, Inc., Acton, MA (US)

(72) Inventor: Bradford Sippy, Acton, MA (US)

(73) Assignee: LENNHAM PHARMACEUTICALS, INC., Acton, MA (US)

Reexamination Request:
No. 90/014,868, Sep. 23, 2021

Reexamination Certificate for:
Patent No.: 11,000,534
Issued: May 11, 2021
Appl. No.: 17/117,916
Filed: Dec. 10, 2020

Related U.S. Application Data

(60) Provisional application No. 63/106,662, filed on Oct. 28, 2020, provisional application No. 63/089,396, filed on Oct. 8, 2020.

(51) Int. Cl.
*A61K 31/675* (2006.01)
*A61K 31/4045* (2006.01)

(52) U.S. Cl.
CPC ........ *A61K 31/675* (2013.01); *A61K 31/4045* (2013.01)

(58) Field of Classification Search
None
See application file for complete search history.

(56) References Cited

To view the complete listing of prior art documents cited during the proceeding for Reexamination Control Number 90/014,868, please refer to the USPTO's public Patent Application Information Retrieval (PAIR) system under the Display References tab.

*Primary Examiner* — Ling X Xu

(57) ABSTRACT

Provided herein are pharmaceutical compositions comprising deuterated derivatives of psilocybin. The provided compositions may be useful for treating and/or preventing various diseases and conditions, such as mood or psychiatric disorders.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 7-12 are determined to be patentable as amended.

Claims 2-6, dependent on an amended claim, are determined to be patentable.

1. A pharmaceutical composition comprising a deuterated compound of Formula (IA-2)[or (IA-3)]:

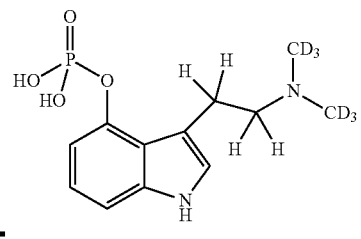

(IA-2)

[

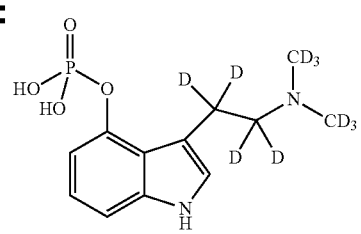

(IA-3)

]

or a pharmaceutically acceptable salt, prodrug, hydrate, or solvate thereof,

*wherein atoms designated H represent predominantly protium isotopes; and* wherein the pharmaceutical composition comprises about 0.5 mg to 500 mg of the compound of Formula (IA-2)[or (IA-3)].

7. The composition of claim 1, wherein the composition comprises about 0.5 mg to about 250 mg of the deuterated compound of Formula (IA-2)[or (IA-3)], or a pharmaceutically acceptable salt thereof.

8. The composition of claim 7, wherein the composition comprises about 0.5 mg to about 50 mg of the deuterated compound of Formula (IA-2)[or (IA-3)], or a pharmaceutically acceptable salt thereof.

9. The composition of claim 8, wherein the composition comprises about 10 mg to about 50 mg of the deuterated compound of Formula (IA-2)[or (IA-3)], or a pharmaceutically acceptable salt thereof.

10. The composition of claim 2, wherein the composition comprises about 0.01 mg/ml to about 50 mg/ml of the deuterated compound of Formula (IA-2)[or (IA-3)], or a pharmaceutically acceptable salt thereof.

11. The composition of claim 1, wherein the composition comprises the deuterated compound of Formula (IA-2)[or (IA-3)], or a pharmaceutically acceptable salt or prodrug thereof.

12. The composition of claim 1, wherein the composition comprises the deuterated compound of Formula (IA-2[or (IA-3)], or a pharmaceutically acceptable salt thereof.

* * * * *